(12) United States Patent
Lee

(10) Patent No.: US 11,458,500 B2
(45) Date of Patent: Oct. 4, 2022

(54) FOCUSED ULTRASONIC ATOMIZER

(71) Applicant: BLOOMY LOTUS LIMITED, HK (CN)

(72) Inventor: Leander Lee, New York, NY (US)

(73) Assignee: BLOOMY LOTUS LIMITED, Central (HK)

( * ) Notice: Subject to any disclaimer, the term of this patent is extended or adjusted under 35 U.S.C. 154(b) by 0 days.

(21) Appl. No.: 17/000,706

(22) Filed: Aug. 24, 2020

(65) Prior Publication Data

US 2022/0055061 A1 Feb. 24, 2022

(51) Int. Cl.
  *B05B 17/06* (2006.01)
  *A61L 9/14* (2006.01)
  *B05B 7/00* (2006.01)

(52) U.S. Cl.
  CPC ............ *B05B 17/0676* (2013.01); *A61L 9/14* (2013.01); *B05B 7/0012* (2013.01); *A61L 2209/132* (2013.01)

(58) Field of Classification Search
  CPC ..... B05B 17/0676; B05B 7/0012; A61L 9/14; A61L 2209/132
  See application file for complete search history.

(56) References Cited

U.S. PATENT DOCUMENTS

| 4,410,139 | A | * | 10/1983 | Nishikawa | .......... | B05B 17/0615 |
| | | | | | | 239/102.2 |
| 8,136,478 | B2 | * | 3/2012 | Buchner | ............ | H01L 21/6715 |
| | | | | | | 118/695 |
| 2003/0197068 | A1 | * | 10/2003 | Abate | ................. | A61M 11/002 |
| | | | | | | 239/338 |
| 2017/0281821 | A1 | * | 10/2017 | Davis, II | ................... | A61L 9/14 |
| 2019/0321849 | A1 | * | 10/2019 | Zu | ............................ | B05B 1/002 |
| 2020/0096213 | A1 | * | 3/2020 | Liang | ....................... | F24F 6/12 |

FOREIGN PATENT DOCUMENTS

CN 108472401 A 8/2018

* cited by examiner

*Primary Examiner* — Qingzhang Zhou
(74) *Attorney, Agent, or Firm* — Hamre, Schumann, Mueller & Larson, P.C.

(57) ABSTRACT

An atomizer device can include a container for storing liquid for atomization, the container defining a top portion and a bottom portion, the top portion defining a mist opening. An ultrasonic transducer can be located at the bottom portion of the container and configured to generate waves in the liquid. A sleeve can extend from the bottom portion toward the top portion of the container. The sleeve can be configured to direct the waves along a longitudinal axis of the sleeve. A float can be located within the sleeve and be configured to move along the longitudinal axis of the sleeve. The float can define a through hole, wherein the waves are concentrated toward a surface of the liquid by passing through the through hole.

13 Claims, 5 Drawing Sheets

FOCUSED ULTRASONIC ATOMIZER

TECHNICAL FIELD

The present disclosure relates to the field of atomizers, and more particularly to ultrasonic atomizers.

BACKGROUND

In daily life, essential oils are often used to improve the surrounding environment or to perform medical treatment, such as sterilization, disinfection or changing environmental odor, etc. When using the essential oils, an atomizer is often used to atomize the essential oils for facilitating diffusion of the essential oils into the environment.

SUMMARY

One aspect of the present disclosure relates to an atomizer device including a container for storing liquid for atomization, wherein the container can define a top portion and a bottom portion and the top portion can define a mist opening, an ultrasonic transducer located at the bottom portion of the container and configured to generate waves in the liquid, and a sleeve extending from the bottom portion toward the top portion of the container and having a longitudinal axis, with the sleeve being configured to direct the waves along the longitudinal axis.

In some embodiments, a float can be located within the sleeve and can be configured to move along the longitudinal axis of the sleeve. The float can define a through hole, wherein the waves can be concentrated toward a surface of the liquid by passing through the through hole. The atomizer device can further include a splash cover located at the top portion of the container and configured to prevent liquid from exiting the mist opening. The splash cover can be attached to at least one of the container or the sleeve.

In some embodiments, the ultrasonic transducer can configured to atomize liquid at a depth of about 55 mm, such as when operating at 24V. The sleeve can define slits configured to allow liquid to enter the sleeve. An output of atomized liquid can be substantially equal across a plurality of operating depths per unit time. The ultrasonic transducer can oscillate in the vertical direction. A liquid depth inside the sleeve can be the same as a liquid depth outside of the sleeve.

In some embodiments, the hole defined by the float tapers upward along the longitudinal axis. An outer diameter of the float can be less than inner diameter of sleeve. The mist opening, the splash cover, the float, and the ultrasonic transducer can be centered along the longitudinal axis of the sleeve. The splash cover can prevent the float from exiting the sleeve. The sleeve can partially constrain the waves from expanding beyond a predetermined radius from the longitudinal axis.

Another aspect of the disclosure relates to an ultrasonic atomizer including a container for storing liquid, a piezoelectric transducer configured to propagate vibrations in the liquid, and a guide wall positioned in the container and configured to constrain the vibrations.

In some embodiments, the atomizer further includes a cover configured to couple with the container to define an internal volume for storing the liquid, the cover defining an aperture for expelling atomized liquid, and a float defining a through hole configured to concentrate the vibrations toward a surface of the liquid, the float being constrained by the guide wall.

In some embodiments, the guide wall constrains the vibrations from expanding beyond a projection of the piezoelectric transducer. The piezoelectric transducer and the guide wall can be offset from a central axis of the container. The atomizer can further include a floating nozzle that defines a hole that opens at a surface of the liquid across a plurality of liquid depths.

The above summary of the present invention is not intended to describe each embodiment or every implementation of the present invention. The Figures and the detailed description that follow more particularly exemplify one or more preferred embodiments.

BRIEF DESCRIPTION OF THE DRAWINGS

The accompanying drawings and figures illustrate a number of exemplary embodiments and are part of the specification. Together with the present description, these drawings demonstrate and explain various principles of this disclosure. A further understanding of the nature and advantages of the present invention may be realized by reference to the following drawings. In the appended figures, similar components or features may have the same reference label.

Figure 1:
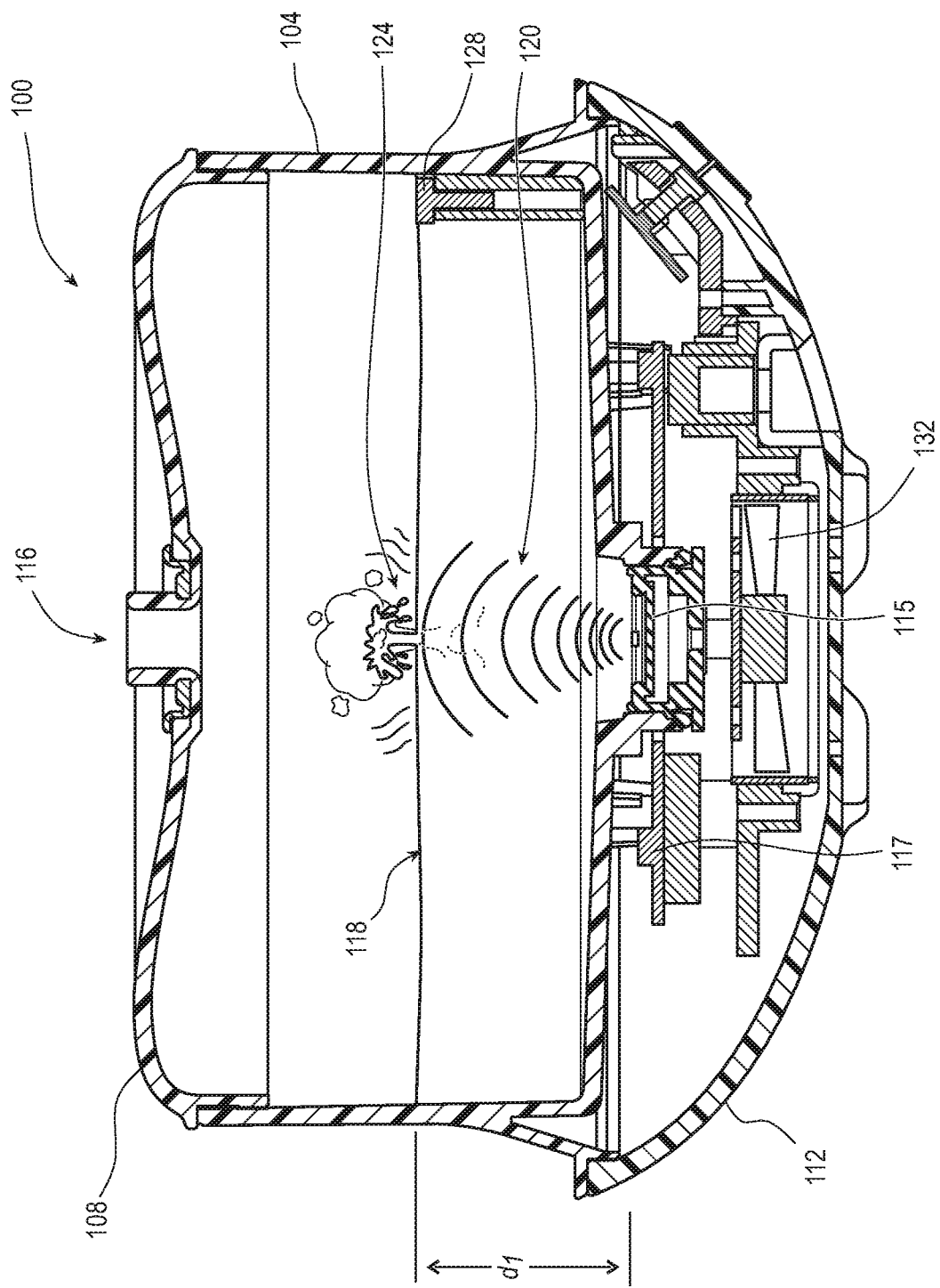
FIG. 1 is a cross-sectional side view of an ultrasonic atomizer according to one embodiment.

While the embodiments described herein are susceptible to various modifications and alternative forms, specific embodiments have been shown by way of example in the drawings and will be described in detail herein. However, the exemplary embodiments described herein are not intended to be limited to the particular forms disclosed. Rather, the instant disclosure covers all modifications, equivalents, and alternatives falling within the scope of the appended claims.

DETAILED DESCRIPTION

The working principle of ultrasonic atomization involves positioning a transducer at the bottom of the tank or container configured to hold liquid. A printed circuit board assembly can be communicatively coupled with the transducer and can apply electrical energy to the transducer. In response to the electrical energy, the transducer can oscillate to generate vibrations or waves in the liquid. In some embodiments, the transducer oscillates in the vertical direction, which in turn propagates waves in the vertical direction. Under the proper depth, the energy propagation produces a liquid column at the surface, and a large number of tiny tension waves occur at the top of the liquid column, greatly reducing surface tension. Once the amplitude of the capillary waves reaches a critical height, they become too tall to support themselves and tiny droplets fall off the tip of each wave into the air to form a mist, resulting in atomization of the liquid.

However, the energy produced by the transducer can be attenuated, absorbed, or diffused, resulting in variations in the energy transmitted to the liquid surface at different liquid depths, which affects the amount of atomization. Thus, traditional ultrasonic aromatherapy devices are limited in that the depth of the liquid is highly restricted to ensure proper performance of the device. For example, the liquid depth of a 24V ultrasonic aromatherapy machine usually cannot exceed around 38 mm, and the liquid depth of a 5V ultrasonic aromatherapy machine usually cannot exceed around 20 mm. Thus, conventional ultrasonic atomizers are restricted in the amount of liquid that is able to be contained in the device. Additionally, conventional atomizers experience a large variance in the amount of mist generated when the liquid depth is large versus when the liquid depth is small. The present disclosure introduces a device capable of overcoming the limitations and shortcomings of conventional ultrasonic atomizers. For instance, many of the complications that arise due to attenuation can be overcome by introducing one or more of the focusing or concentrating features as disclosed herein.

It will be appreciated that while the present disclosure focuses on essential oil atomizers, the components and principles discussed herein can be applied to a wide range of fields, such as spray painting, humidifiers, electronic cigarettes, fuel cells, wafers, solar panels, similar devices, and combinations thereof.

FIG. 1 illustrates a cross-sectional side view of an ultrasonic atomizer 100 according to one embodiment. The atomizer 100 includes a tank or container 104 configured to hold liquid. As used herein "liquid" can refer to a wide variety of liquid substances that are capable of being atomized, such as essential oils, water, other aromatic fluids, and combinations thereof. The tank 104 can be positioned on a base 112 configured to house various operational components such as a fan 132, electrical components, and a printed circuit board assembly. The fan 132 can be used to direct atomized mist or vapor away from the atomizer 100 and into the air. The atomizer 100 can further include a cover or lid 108 configured to couple with the tank 104 to form a volume within which the liquid is stored. The cover 108 can define a mist opening or aperture 116. The opening 116 allows atomized mist to escape the internal volume defined by the tank 104 and cover 108 and enter into the outside environment. The atomizer 100 can include an ultrasonic transducer 115. In some examples, the transducer 115 can be a piezoelectric transducer. The transducer 115 can be incorporated into a bottom of the tank 104 such that at least a portion of the transducer 115 is in contact with fluids held in the internal volume of the tank 104. In some embodiments, the transducer 115 can comprise a protective layer or fluid-tight layer separating delicate components of the transducer 115 from the fluid while allowing vibrations generated by the transducer 115 to pass into the fluids of the tank 104.

A printed circuit board assembly 117 can be communicatively coupled with the transducer 115 and can apply electrical energy to the transducer 115. In response to the electrical energy, the transducer 115 can oscillate to generate vibrations or waves 120 in the liquid. In some embodiments, the transducer 115 oscillates in the vertical direction, which in turn, generates pulses or waves 120 that propagate in the vertical direction (i.e., from the bottom of the tank 104 toward the cover 108). Under the proper liquid depth, and with the proper vibration strength and frequency, the vibrational waves can produce a liquid column 124 at the surface 118, resulting in atomization of the liquid. In some embodiments, the atomizer 100 can be configured such that the ultrasonic transducer 115 is configured to atomize liquid at a depth of about 38 mm when operating at 24V. A depth indicator 128 can be attached or formed into the tank 104 to prevent overfilling the tank 104. The depth indicator 128 can serve as a visual reference of the max fill line for the user. In some embodiments, the depth indicator 128 includes an overspill reservoir to prevent overfilling the tank 104 which can reduce the effectiveness of the atomization. For example, the atomizer 100 may only be able to atomize liquid when the liquid depth is no greater than a depth $d_1$. A top-most position the depth indicator 128 in the tank 104 can be substantially equal to the top of the depth $d_1$.

Figure 2:
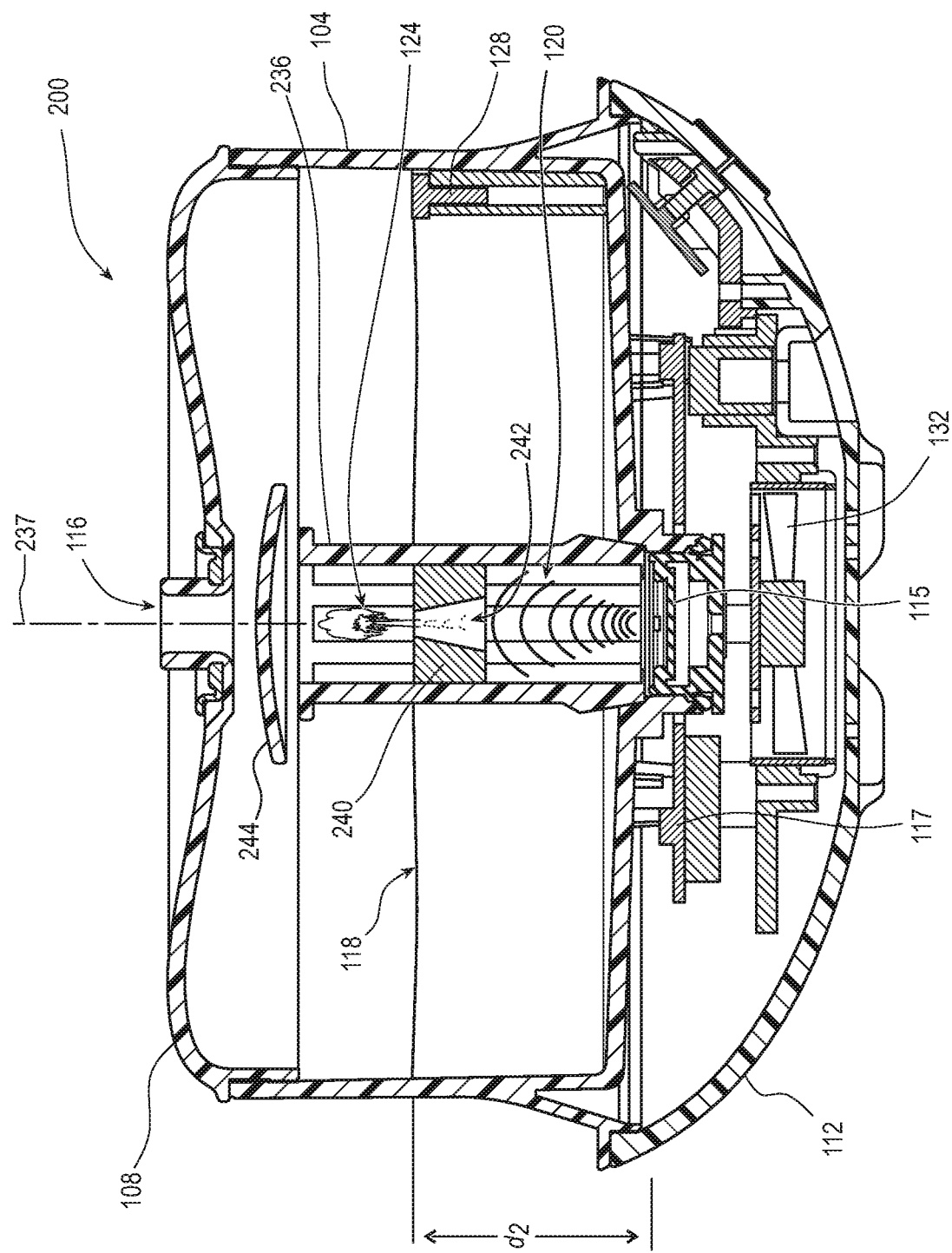
FIG. 2 is a cross-sectional side view of an ultrasonic atomizer including focusing features.

FIG. 2 illustrates a side cross-sectional view of a focused ultrasonic atomizer 200 according to one embodiment. The atomizer 200 can be substantially similar to, and can include some or all of the features of, the atomizer 100 discussed above. For instance, the atomizer 200 can include a tank 104, cover 108, and base 112.

Figure 3:
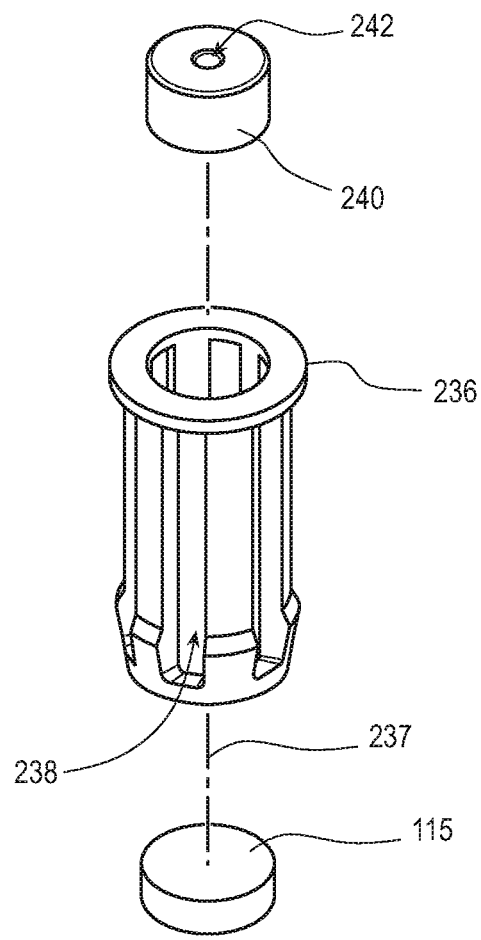
FIG. 3 is partially exploded perspective view of a transducer, a sleeve, and a float of the ultrasonic atomizer of FIG. 2.

In some embodiments, the atomizer 200 can include a guide, baffle, or sleeve 236 positioned in the tank 104. The sleeve 236 can have an inner surface configured to come into contact with the waves 120 produced by the transducer 115 as they radiate through the fluid in the tank 104. The sleeve 236 can be shaped and/or positioned to concentrate or reflect the waves 120. For instance, the sleeve 236 can be configured to restrict or constrain the waves 120 such that the waves 120 are directed upward along the sleeve 236 toward the surface of the liquid. In this manner, the sleeve 236 at least partially constrains the propagation of the waves 120 from expanding beyond a predetermined radius from the longitudinal axis 237, wherein the radius is defined by the inner radius of the sleeve 236. In some embodiments, the sleeve 236 can completely constrain the waves 120 from propagating laterally beyond the inner radius of the sleeve 236. In other words, the waves can be driven into the inner surface of the sleeve 236 and can be at least partially reflected or absorbed by the sleeve such that along at least a portion of the longitudinal length of the sleeve 236, the waves do not significantly escape the sleeve 236 or pass unhindered into the remaining liquid in the tank 104. In some embodiments, only a portion of the waves 120 are constrained by the sleeve 236, while some of the waves 120 propagate beyond the internal radius of the sleeve 236, for example, through slits 238, as discussed below with reference to FIG. 3. As stated above, the energy produced by traditional ultrasonic atomizers can be attenuated, absorbed, or diffused, resulting in variations in the energy transmitted to the liquid surface at different liquid depths, which affects the amount of atomization. In some cases, when the liquid depth exceeds a maximum operating depth, the energy is attenuated to such a degree that the transducer is unable to atomize the liquid. To overcome these shortcomings, the sleeve 236 acts as a focusing barrier and prevents at least portions of the waves 120 from being dissipated or attenuated outside of the sleeve 236. Thus, the sleeve 236 can reduce the attenuation of the vibrational energy during propagation through the liquid. This focusing or concentrating of the waves 120 can greatly amplify the amount of atomization because the sleeve 236 reduces attenuation and dispersion of the waves 120 throughout the tank 104 external to the sleeve 236, thereby greatly amplifying the tension wave concentrated at the top of the water column 124 to increase the amount of atomization.

The sleeve 236, as shown in FIGS. 2 and 3, can be a hollow tube. It will be understood that the sleeve 236 is not limited to the particular embodiment depicted in the figures. For example, the sleeve or guide 236 is not necessarily cylindrical and may be rectangular, hexagonal, elliptical, or may take on another shape. In some embodiments, the sleeve 236 can be referred to as a guide wall, working in combination with a sidewall of the tank 104 to direct propagation of the waves 120. As shown in FIG. 3, the sleeve 236 can define one or more slits, gaps, holes, or other openings 238 to allow the liquid to enter the sleeve 236 through the slits 238. As a result, the surface of the liquid level inside the sleeve 236 can be maintained at substantially the same level as outside the sleeve 236 within the tank 104. In other words, the surface height of the liquid outside of the sleeve is the same as the surface height of the liquid inside of the sleeve 236. As a result, the depth of the liquid within the sleeve 236 and the rest of the tank 104 remains consistent, and the fluid within the sleeve 236 does not run out before the rest of the tank 104 (or vice versa). In some embodiments, the sleeve 236 is stationary relative to the tank 104 and transducer 115. For example, the sleeve 236 can be attached, either permanently or removably to a portion of the tank 104. In some embodiments, the sleeve 236 can be securely attached to the transducer 115 which in turn is attached to the tank 104 and/or to the base 112. In some embodiments, the position of the sleeve 236 remains the same, regardless of the liquid depth level. In some embodiments, the sleeve 236 can comprise a continuous inner surface about its circumference, wherein no slits 238 interrupt the inner surface, and, rather than having slits 238, a plurality of apertures or channels are located at the base of the sleeve 236 to permit passage of fluid into the base of the inner chamber of the sleeve 236. In this manner, the waves generated by the transducer 115 can be especially highly concentrated by the sleeve 236 since they can be substantially entirely contained within the central fluid column within the sleeve 236.

In some embodiments, the atomizer 200 includes a float or nozzle 240. The float 240 can be buoyant so that it floats on or near the surface 118 of the liquid. The float 240 can be positioned inside the sleeve 236. For instance, the float 240 can have a periphery cross section that has the same cross-sectional shape as the internal walls of the sleeve 236. In some embodiments, an outermost diameter of the float 240 is less than an innermost diameter of the sleeve 236 such that the float 240 can freely move along the longitudinal axis 237 of the sleeve. In other words, a slight gap can exist between the outer peripheral surface of the float 240 and the inner wall surface(s) of the sleeve 236 to ensure that the float 240 can move freely in the sleeve 236 along the longitudinal axis of the sleeve 236. The float 240 can be configured to fit securely in the sleeve 236 such that the float 240 cannot travel in the horizontal direction. Accordingly, as the fluid level in the tank 104 changes, the float 240 can remain at the top surface of the fluid level over time.

As shown in FIG. 3, the transducer 115, the sleeve 236, and the float 240 can be centered along the longitudinal axis 237. The sleeve 236 can define an internal volume within which the float 240 resides. In some embodiments, at least a portion of the float 240 can extend into one or more of the slits 238 to restrict rotation of the float 240 along the longitudinal axis 237. In some embodiments, the float 240 can rotate within the sleeve 236 about the longitudinal axis 237. The slits 238 can be wide enough to allow the liquid to freely enter the sleeve 236, yet narrow enough such that the float 240 remains secured within the sleeve 236. The slits 238 can also be configured to have opening widths that enable the fluid in the tank 104 to freely circulate around the tank 104 and interior of the sleeve 236 so that the fluid being atomized has a generally consistent mix ratio (e.g., when a mixture of water and oil are atomized).

The float 240 can include a through hole or aperture 242 that extends through the float 240. The through hole 242 can be any shape, for example, the through hole 242 can be a circular or conical through hole in the middle of the float 240 for constraining and focusing waves of vibrational energy travelling through the liquid. In some embodiments, the through hole 242 is tapered upward (i.e, toward the cover 108), such that a lower diameter of the through hole 242 is larger than an upper diameter of the through hole 242. The tapered through hole 242 can be configured to concentrate or focus the waves 120 as they propagate upward through the float 240. Thus, the waves can agitate the fluid at the surface 118 more powerfully than if there had been no float 240.

The float 240 can be made of a buoyant material. For example, the float 240 can have a buoyancy sufficient to position a top surface of the float 240 substantially in plane or flush with the surface of the liquid (i.e., the float 240 can be substantially submerged while remaining near the surface of the liquid). In some examples, the float 240 can have a buoyancy sufficiently high to cause the float 240 to sit atop the surface 118 of the liquid (i.e., with a majority of the float 240 above the surface of the liquid). In any case, the buoyancy of the float 240 can enable the float 240 to remain at the surface 118 irrespective of the amount of liquid in the tank 104. This property can help ensure more consistent atomization of the liquid, whether the tank is full or nearing empty.

In some embodiments, the longitudinal axis of the sleeve 236 is aligned with a center of the transducer 115 such that the through hole 242 in the float 240 and the center of the transducer 115 are on roughly the same axis (i.e., the longitudinal axis of the sleeve 236).

The incorporation of the sleeve 236 and/or the float 240 can allow for an increase of at least 70% in the liquid depth. For instance, the ultrasonic transducer 115 can be configured to atomize liquid at a depth of about 55 mm when operating at 24V (as compared to a conventional ultrasonic atomizer, which can only effectively atomize up to 38 mm of liquid depth at 24V). Further, because the sleeve 236 and/or the float 240 cause an energy focusing effect, the atomizer can output atomized droplets at a much more consistent rate, even with drastic changes in the liquid depth. Thus, an output of atomized liquid can be substantially equal across a plurality of operating depths.

Due to the advantageous effects of the sleeve 236 and/or float 240, the atomizer 200 has a greater maximum operating depth $d_2$ than the maximum operating depth $d_1$ of the atomizer 100. Advantageously, this allows a user to beneficially operate the atomizer 200 with a greater amount of liquid in the tank 104 than would be possible in the atomizer 100. Consequently, the atomizer 200 requires the tank 104 to be refilled less than the atomizer 100, and an equal rate of atomization can be achieved for a longer duration. Further, such a configuration reduces energy demands of the transducer 115 by more efficiently transferring the vibrational energy to the surface 118.

In some examples, the atomizer 200 includes a splash guard 244 positioned between the sleeve 236 and the cover 108. The splash guard 244 can be configured to block liquid from exiting the opening 116, while still allowing atomized mist to exit the opening 116. In some embodiments, the splash guard 244 is attached to the cover 108 by means of any suitable attachment mechanism (e.g., fasteners, tabs, threads, etc.). In some embodiments, the splash guard 244 is integrally formed with the cover 108. For instance, the splash guard 244 and the cover 108 can be formed from a single mold and as a single, integral piece. The splash guard 244 can prevent the float 240 from exiting the sleeve 236. For instance, the splash guard 244 can be separated from the top of the sleeve 236 by a distance that is less than a height of the float 240 such that the float 240 comes into mechanical interference with the splash guard 244 before the float 240 is able to become dislodged from the sleeve 236.

Figure 4:
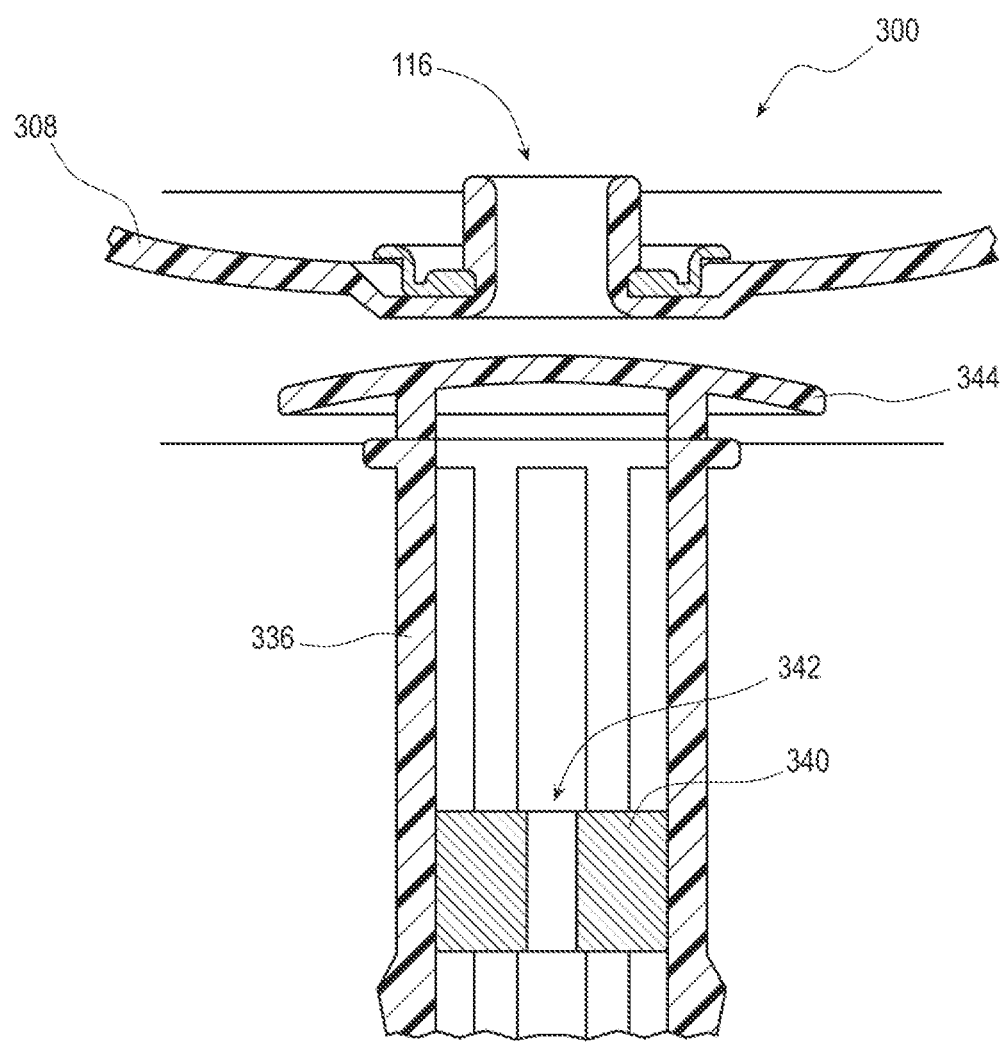
FIG. 4 is an enlarged cross-sectional side view of a sleeve and float according to one embodiment.

FIG. 4 illustrates a cross-sectional side view of an atomizer 300 according to one embodiment. The atomizer 300 can be substantially similar to, and include some or all of the features of atomizers 100 and 200 discussed above. Certain components of the atomizer 300 have been removed for clarity. In some embodiments, the atomizer 300 can include a splash guard 344 that is substantially similar to the splash guard 244 in shape, but which is coupled or affixed to the sleeve 336 rather than the cover 308. It will be understood that despite being affixed to the sleeve 336, the splash guard 344 and sleeve 336 still permit atomized mist to escape the atomizer 300 while preventing liquid from splashing out of the opening 116. For example, the mist and vapor can exit the sleeve 336 between slits in the sleeve 336 or through openings (not shown) formed between the sleeve 336 and the splash guard 344. In some examples, the splash guard 344 can be attached to both the sleeve 336 and the cover 308.

FIG. 4 further illustrates a float 340. The float 340 can be substantially similar to the float 240 with the exception that the float 340 defines a cylindrical through hole 342 rather than the conical though hole 242 illustrated in FIG. 2. In this manner, less energy can be concentrated toward the top end of the float 340 as compared to float 240. The inner diameter and cross-section of the through holes 242, 342 can also be modified to control the rate of atomization through the float, such as by increasing the inner diameter of the through holes 342 to allow more dispersed energy to pass through the float.

As illustrated in FIGS. 2-4, the mist opening 116, the splash guard 244, the float 240, and the ultrasonic transducer 115 can each be centered and aligned along the longitudinal axis 237 of the sleeve 236, and further, in some embodiments, can be centered along a central axis of the tank 104. However, it will be understood that other configurations are also possible. For instance, in some embodiments, the splash guard 244 and/or the mist opening 116 can be offset from the longitudinal axis 237 of the sleeve 236.

Figure 5:
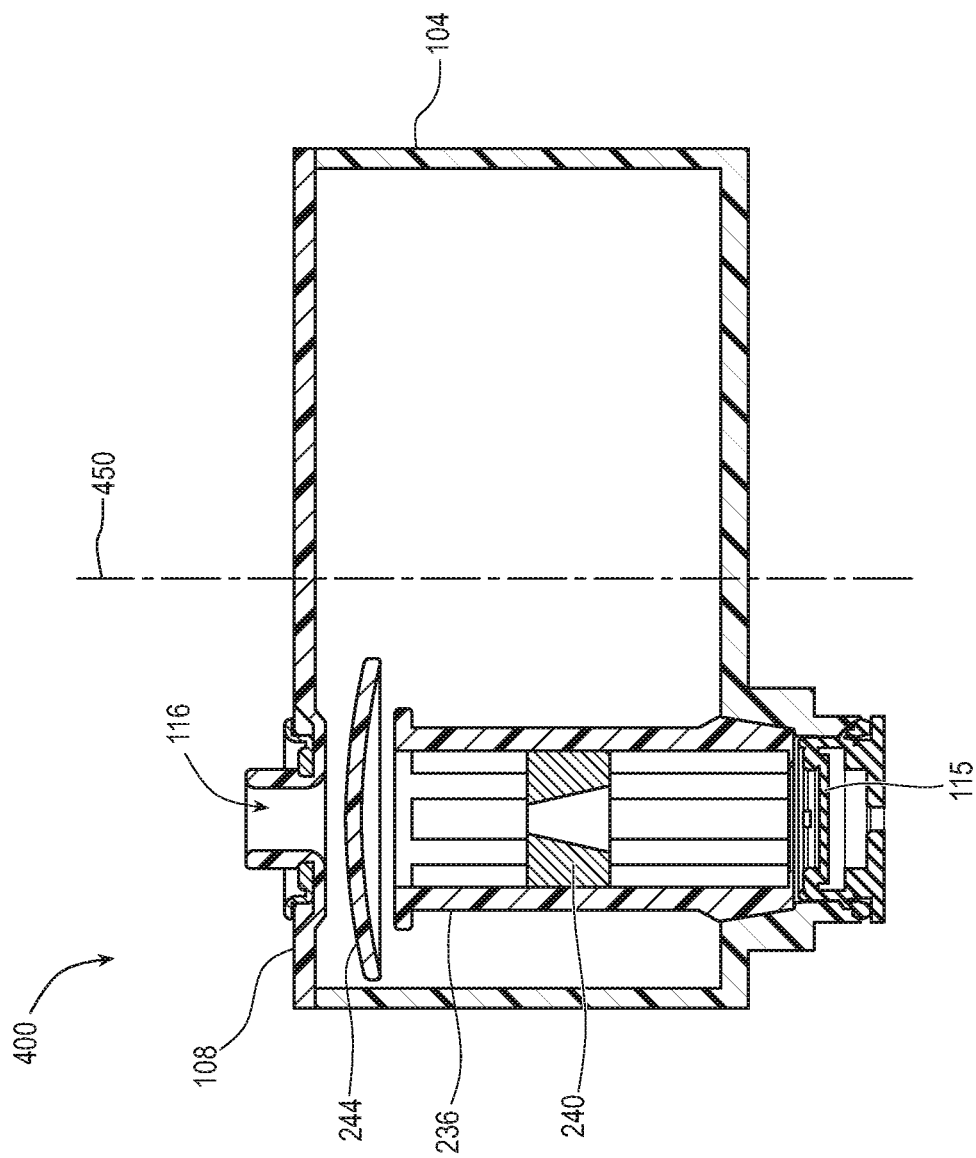
FIG. 5 is a cross-sectional side view of an ultrasonic atomizer with an offset atomizing assembly.

FIG. 5 illustrates a diagrammatic side cross-section view of an atomizer 400 including an off-axis, asymmetrical atomization assembly. The atomizer 400 can be substantially similar to, and include many of the parts of atomizers 100, 200, and 300 configured to perform their respective functions. Thus, certain components of the atomizer 400 have been removed for clarity in FIG. 5. In some embodiments, at least one of the transducer 115, the sleeve 236, the float 240, the splash guard 244, or the mist opening 116 can be offset from a central axis 450 bisecting the tank 104. Because of the isolated atomization region created by the sleeve 236, the transducer 115 can still effectively atomize the liquid despite being off-axis. This can remain true even when the sleeve is substantially proximate a sidewall of the tank 104. An asymmetrically-located atomization column (including at least sleeve 236, float 240, and cover 244) can enable the atomizer 400 to have different aesthetic designs, to incorporate multiple atomization columns (e.g., one on the left side and one on the right side of the tank 104), to make it easier for the user to fill the tank (e.g., because most of the tank is empty), and to make it easier to repair or replace parts of the atomizer 400 (e.g., because parts can be located near outer surfaces of the container for easier access).

It is noted that when a component is referred to as being "fixed to," "installed on," "arranged on" or "disposed on" another component, it can be directly or indirectly fixed on another component. When a component is referred to as being "connected to" another component, it can be directly or indirectly connected to the other component.

In addition, the terms "first" and "second" are for illustrative purposes only and should not be construed as indicating or implying a relative importance or indicating the quantity of technical features. Therefore, a feature that is qualified as "first" and "second" may expressly or implicitly include one or more of such a feature. In the description of the present invention, "multiple" means two or more, unless otherwise specifically defined.

Unless specified otherwise, it should be understood that, "length", "width", "upper", "lower", "front", "back", "left" and "right", "vertical", "horizontal", "top", "bottom", "inside", "outside" and other terms indicating the orientation or positional relationship are used to refer to orientation or positional relationship shown in the drawings, only for the purpose of facilitating and simplifying the description of the invention, instead of indicating or implying that the indicated device or component must have a specific orientation and constructed and operated in a particular orientation, and therefore cannot be construed as limiting.

In the description of the present invention, it should be noted that the terms "install," "connected," and "connect" should be interpreted broadly unless specifically defined or limited otherwise. For example, the components may be fixedly connected or they may be detachable connected, or integral connected. The connection can be mechanical or electrical. The connection can be direct or indirect (connected through an intermediary). It can also be the internal communication of two components or the interaction between two components. Those of ordinary skill in the art can understand the specific meanings of the above terms in the present disclosure according to specific circumstances.

The present description provides examples, and is not limiting of the scope, applicability, or configuration set forth in the claims. Thus, it will be understood that changes may be made in the function and arrangement of elements discussed without departing from the spirit and scope of the disclosure, and various embodiments may omit, substitute, or add other procedures or components as appropriate. For instance, the methods described may be performed in an order different from that described, and various steps may be added, omitted, or combined. Also, features described with respect to certain embodiments may be combined in other embodiments.

Various inventions have been described herein with reference to certain specific embodiments and examples. However, they will be recognized by those skilled in the art that many variations are possible without departing from the scope and spirit of the inventions disclosed herein, in that those inventions set forth in the claims below are intended to cover all variations and modifications of the inventions disclosed without departing from the spirit of the inventions. The terms "including:" and "having" come as used in the specification and claims shall have the same meaning as the term "comprising."

What is claimed is:

1. An atomizer device, comprising:
 a container for storing liquid for atomization, the container defining a top portion and a bottom portion, the top portion defining a mist opening;
 an ultrasonic transducer located at the bottom portion of the container and configured to generate waves in the liquid;
 a sleeve extending from the bottom portion toward the top portion of the container and having a longitudinal axis and a sleeve width, the sleeve configured to direct the waves along the longitudinal axis, the sleeve defining an opening configured to allow liquid to enter the sleeve from the container, the opening extending along a majority of a height of the sleeve; and a splash guard attached to a top end of the sleeve and configured to prevent liquid from exiting the mist opening, the splash guard having an arched top portion and a guard width greater than the sleeve width;

a float located within the sleeve and configured to move along the longitudinal axis of the sleeve;

a second opening defined by the splash guard and the sleeve between the splash guard and sleeve to permit vapor to exit the sleeve;

wherein a distance between the splash guard and the top of the sleeve is less than a height of the float to prevent dislodging of the float from the sleeve.

2. The atomizer device of claim 1, wherein the float defines a through hole, wherein the waves are concentrated toward a surface of the liquid by passing through the through hole.

3. The atomizer device of claim 2, wherein the through hole defined by the float tapers upward along the longitudinal axis.

4. The atomizer device of claim 2, wherein an outer diameter of the float is less than an inner diameter of sleeve.

5. The atomizer device of claim 2, wherein the float and the ultrasonic transducer are aligned along the longitudinal axis of the sleeve.

6. The atomizer device of claim 1, wherein the ultrasonic transducer is configured to atomize liquid at a depth of about 55 mm.

7. The atomizer device of claim 1, wherein an output of atomized liquid is configured to be substantially equal across a plurality of operating depths per unit time.

8. The atomizer device of claim 1, wherein a liquid depth inside the sleeve is configured to be equal to a liquid depth outside of the sleeve.

9. The atomizer device of claim 2, wherein the sleeve is configured to prevent the float from exiting the sleeve.

10. The atomizer device of claim 1, wherein the sleeve partially constrains the waves from expanding beyond a predetermined radius from the longitudinal axis.

11. A method for atomizing liquid, comprising:

providing an ultrasonic transducer at a bottom portion of a container holding a liquid, the ultrasonic transducer being configured to propagate waves toward a surface of the liquid; and positioning a sleeve in the container such that a longitudinal axis of the sleeve corresponds to a propagation direction of the waves, the sleeve configured to at least partially constrain the waves along the longitudinal axis;

positioning a floating nozzle within the sleeve, the floating nozzle defining a tapering opening and having a buoyancy configured to keep a top surface of the floating nozzle and a top end of the tapering opening flush with the surface of the liquid; and attaching a splash guard to the sleeve such that a distance between the splash guard and the top of the sleeve is less than a height of a float to prevent dislodging of the float from the sleeve and an opening defined by the splash guard and the sleeve between the splash guard and sleeve to permit vapor to exit the sleeve;

wherein the splash guard has a greater width dimension than the sleeve.

12. The method of claim 11, wherein the floating nozzle is configured to move along the longitudinal axis of the sleeve, wherein the waves are directed toward a surface of the liquid by passing through the tapering opening.

13. The method of claim 12, wherein the splash guard is positioned between another opening of the container and the sleeve, the splash guard configured to prevent liquid from exiting the container through the another opening.

* * * * *